United States Patent [19]

Saito

[11] Patent Number: 5,118,404
[45] Date of Patent: Jun. 2, 1992

[54] ENZYME ELECTRODE AND A METHOD OF DETERMINING CONCENTRATION OF AN ANALYTE IN A SAMPLE SOLUTION

[75] Inventor: Atsushi Saito, Tokyo, Japan

[73] Assignee: NEC Corporation, Tokyo, Japan

[21] Appl. No.: 660,911

[22] Filed: Feb. 27, 1991

Related U.S. Application Data

[63] Continuation of Ser. No. 514,880, Apr. 26, 1990, abandoned.

[30] Foreign Application Priority Data

Apr. 28, 1989 [JP] Japan .................. 1-107202
Aug. 4, 1989 [JP] Japan .................. 1-201207

[51] Int. Cl.$^5$ .......................................... G01N 27/26
[52] U.S. Cl. .................................. 204/403; 204/415;
204/153.12; 435/288; 435/174; 435/817; 435/14
[58] Field of Search ............... 204/153.12, 403;
357/25; 435/14, 288, 174, 817

[56] References Cited

U.S. PATENT DOCUMENTS

| | | | |
|---|---|---|---|
| 4,307,195 | 12/1981 | Karasawa et al. | 435/288 |
| 4,547,280 | 10/1985 | Karasawa et al. | 204/403 |
| 4,552,840 | 11/1985 | Riffer | 435/14 |
| 4,655,880 | 4/1987 | Liu | 204/153.12 |
| 4,832,797 | 5/1989 | Vadgama et al. | 204/153.12 |
| 4,839,000 | 6/1989 | Eddowes | 204/153.12 |
| 4,890,620 | 1/1990 | Gough | 128/635 |
| 4,900,423 | 2/1990 | Iida et al. | 204/403 |

Primary Examiner—John Niebling
Assistant Examiner—Bruce F. Bell
Attorney, Agent, or Firm—Laff, Whitesel, Conte & Saret

[57] ABSTRACT

An enzyme electrode usable for determining high concentration of analyte in a sample solution is provided, by providing an enzyme-immobilized membrane in the electrode with pH buffer capacity. Durability of the electrode can be improved by using albumin crosslinked by glutaraldehyde as a permeation-restricted membrane in the electrode. Method of using the electrode can be simplified by introducing a stirring step, measuring outputs before and after the stirring step and utilizing difference of measured outputs.

5 Claims, 4 Drawing Sheets

ENZYME ELECTRODE AND A METHOD OF DETERMINING CONCENTRATION OF AN ANALYTE IN A SAMPLE SOLUTION

This application is a continuation of application Ser. No. 07/514,880, filed Apr. 26, 1990, now abandoned.

BACKGROUND OF THE INVENTION

1. Field of the Invention

The present invention relates to an enzyme electrode and a method of determining concentration of an analyte in a sample solution by means of the enzyme electrode.

2. Description of the Prior Art

Many reports have been made up to the present day on an enzyme electrode comprising an electrochemical transducer device for detecting variation of phase boundary potential and an enzyme-immobilized membrane provided on the surface of the electrochemical transducer device.

For example, as to the enzyme electrode wherein glucose oxidase is immobilized as the enzyme, that is, a glucose sensor, there are many embodiments already reported, such as those described in "Biophysica Biochimica Acta", Vol. 320 (1973), pages 529-534 and "Analytical Chemistry", Vol. 57 (1985), pages 1917-1925. Each of these sensors relies upon a principle that glucose produces gluconic acid by catalytic action of glucose oxidase and the thus produced gluconic acid can be determined by measuring pH variation. The reaction procedures to produce gluconic acid from glucose may be shown as follows:

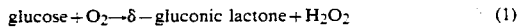

$$\text{glucose} + O_2 \rightarrow \delta-\text{gluconic lactone} + H_2O_2 \quad (1)$$

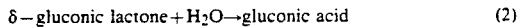

$$\delta-\text{gluconic lactone} + H_2O \rightarrow \text{gluconic acid} \quad (2)$$

The reaction (1) is catalyzed by glucose oxidase and the reaction (2) proceeds spontaneously or by catalytic action of gluconolactonase.

In the above mentioned glucose sensors, oxygen is required for operating them. Ordinarily, oxygen dissolved in the solution to be determined is used, but its concentration is to an extent of 0.25 mM in the case of saturation by atmosphere and of 1.2 mM in the case of saturation by oxygen gas and so is not sufficient for determining high concentration of glucose. Therefore, in order to determine high concentration of glucose, heretofore, a sample solution was diluted by a buffer solution and then determination was made. It was proposed, in order to make determination without such dilution, to use a glucose sensor which comprises an enzyme electrode, an enzyme-immobilized membrane and a permeation-restricted membrane, which has restricted permeability to glucose but has good permeability to oxygen, provided on the enzyme electrode, in Japanese Patent Appln. No. 5,171/1987. It was considered that by the merit of such permeation-restricted membrane, concentration of oxygen in the enzyme-immobilized membrane became high relatively to glucose concentration, and thus it would be possible to determine high concentration of glucose.

On the other hand, it is required in a glucose sensor utilizing an electrochemical transducer device detecting variation of phase boundary potential, particularly variation of hydrogen-ion concentration of a solution, that the solution to be analyzed has a constant or a known pH buffer capacity on a surface of the transducer device, in order to determine glucose concentration. The above permeation-restricted membrane however does not readily permeate molecules of substances which have pH buffer capacity in the solution to be analyzed, and so the enzyme-immobilized membrane is allowed to have only low pH buffer capacity and thus pH value in the enzyme-immobilized membrane is easily changed.

Therefore, in a glucose sensor utilizing an electrochemical transducer device detecting variation of phase boundary potential, the combination only of the enzyme-immobilized membrane and the permeation-restricted membrane is, in fact, not sufficient for determining high concentration of glucose, owing to a phenomenon that pH variation in the enzyme-immobilized membrane becomes larger and so an output of the sensor is saturated even by not so high concentration of glucose. Similar problem occurs in other sensors than the above glucose sensor as long as they require oxygen, such as an alcohol sensor utilizing a similar transducer device in combination with alcohol oxidase.

Further, in a method of determining concentration of an analyte in a sample solution by means of an enzyme electrode, there are problems of a complicated operation due to the fact that background output has to be corrected by immersing the electrode into a buffer solution which is free from glucose and also of a low S/N ratio of obtained signals due to the fact that adsorption of proteins or sudden change of pH value occurs when the electrode is immersed in a solution to be analyzed after the above correction procedure.

SUMMARY OF THE INVENTION

An object of the present invention therefore is to present an enzyme electrode which enables to determine high concentration of an analyte in a sample solution. Another object of the present invention is to present a method of determining concentration of an analyte in a sample solution, which enables to simplify operation of the concentration determining method and to improve S/N ratio of the signals obtained by the concentration determination.

Thus the present invention provides an enzyme electrode comprising:
(a) an electrochemical transducer device for delecting variation of phase boundary potential,
(b) an enzyme-immobilized membrane having pH buffer capacity, and
(c) a permeation-restricted membrane having restricted permeability to an analyte but good permeability to oxygen;
said enzyme-immobilized membrane (b) and permeation-restricted membrane (c) being formed on the surface of said electrochemical transducer device (a) in this order.

The present invention also provides a method of determining concentration of an analyte in a sample solution by means of an enzyme electrode comprising:
(a) an electrochemical transducer device for detecting variation of phase boundary potential, (b) an enzyme-immobilized membrane having pH buffer capacity, and (c) a permeation-restricted membrane having restricted permeability to an analyte but good permeability to oxygen; said enzyme-immobilized membrane (b) and permeation-restricted membrane (c) being formed on the surface of said electrochemical transducer device (a) in this order, which method comprises steps of:

(i) immersing said enzyme electrode in the sample solution for a predetermined time period,
(ii) stirring the sample solution, and
(iii) measuring difference of electrode outputs between before stirring and after the stirring, thereby to determine concentration of the analyte in the sample solution.

In the enzyme electrode of the present invention, a permeation-restricted membrane which has high permeability to oxygen but restricted permeability to an analyte is provided outside an enzyme-immobilized membrane, thereby to produce circumstance that oxygen concentration is sufficiently high relatively to analyte concentration and so an enzyme reaction depends upon the analyte concentration and not upon the oxygen reaction. Further, a membrane having pH buffer capacity is provided inside the enzyme-immobilized membrane or the enzyme-immobilized membrane itself is made to have pH buffer capacity, thereby to maintain pH buffer capacity on a surface of an electrochemical transducer device at a constant level and thus to enable to quantitatively measure signals varying in accordance with pH variation.

In the method of the present invention, determination of analyte concentration is made after immersing an enzyme electrode in a sample solution for a predetermined time period and then after stirring the sample solution, by measuring difference of electrode outputs between before and after the stirring. By this, it becomes possible to make the determination without using a buffer solution for background correction, because before stirring, only small amount of oxygen is dissolved in the sample solution and so an enzyme reaction does not proceed, but after stirring, concentration of the dissolved oxygen is saturated and so the enzyme reaction proceeds to cause pH variation and produce output difference in accordance with analyte concentration.

As for the permeation-restricted membrane, it may be formed by cellulose acetate, polyurethane, silicone, etc. as in the prior art. However, because these materials have not so strong adhesion to surfaces of the enzyme-immobilized membrane and of the electrode, it is recommended to use a material comprising alubumin cross-linked by glutaraldehyde, which has newly been found to have strong adhesion to the surfaces. The use and effect of this material have not been known but are new and so constitute another aspect of the present invention.

As for the immobilized enzyme, it is suitable to use glucose oxidase and gluconolactonase.

As for the electrochemical transducer device for detecting variation of phase boundary potential, it is suitable to use an ion sensitive field effect transistor.

As for the sample solution to be analyzed, it is suitable to employ serum or whole blood.

DESCRIPTION OF THE PREFERRED EMBODIMENTS

The present invention will be explained below further in detail with respect to its some embodiments shown as working examples.

EXAMPLE 1

A glucose sensor was prepared as an embodiment of the enzyme electrode of the present invention, by using an ion sensitive field effect transistor [—ISFET] as the electrochemical transducer device and glucose oxidase as the enzyme, to have constitution as shown in FIG. 1(a) as a cross sectional view.

This glucose sensor was prepared by providing an enzyme-immobilized membrane 2 having pH buffer capacity on a sensing portion of said ISFET 1. The formation of this membrane 2 may in general be made by a lift-off method as described for example in Japanese Patent Appln. No. 209,165/84. As for an enzyme solution, it is possible to use, for example, a solution of a composition as follows:

Bovine serum albumin: 30 mg
50 mM HEPES-Na solution (pH 7.5): 0.8 ml
5% glutaraldehyde aqueous solution: 0.2 ml
Glucose oxidase (ECL. 1. 3. 4, product of Boelinger Mangheim Co., Grad III): 20 mg The membrane thus formed was immersed in 0.1M glutamic acid solution for 10 minutes to introduce carboxyl groups thereinto. A large amount of carboxyl groups could thus be immobilized in the membrane to act as a buffering agent against an acid produced by an enzyme reaction.

Next, silicone solution (Dow Corning's product DKX 4-360-2) is coated on the above buffered enzyme-immobilized membrane to form a permeation-restricted membrane.

Figure 2:
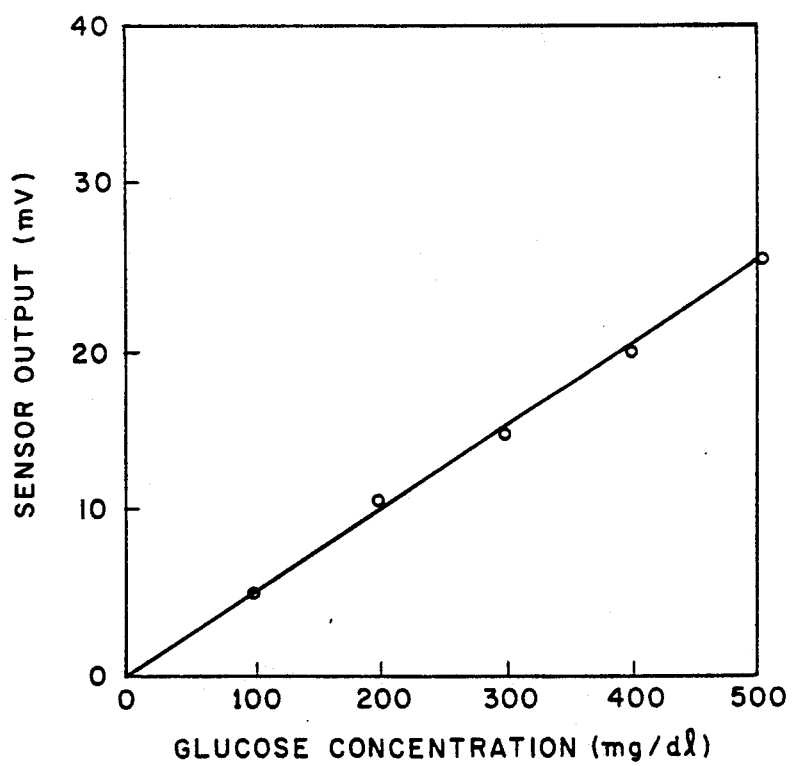
FIG. 2 is a graphic illustration of a calibration line obtained by the glucose sensor of FIG. 1(a) showing dependency of glucose concentration upon output of the glucose sensor.
Figure 3:
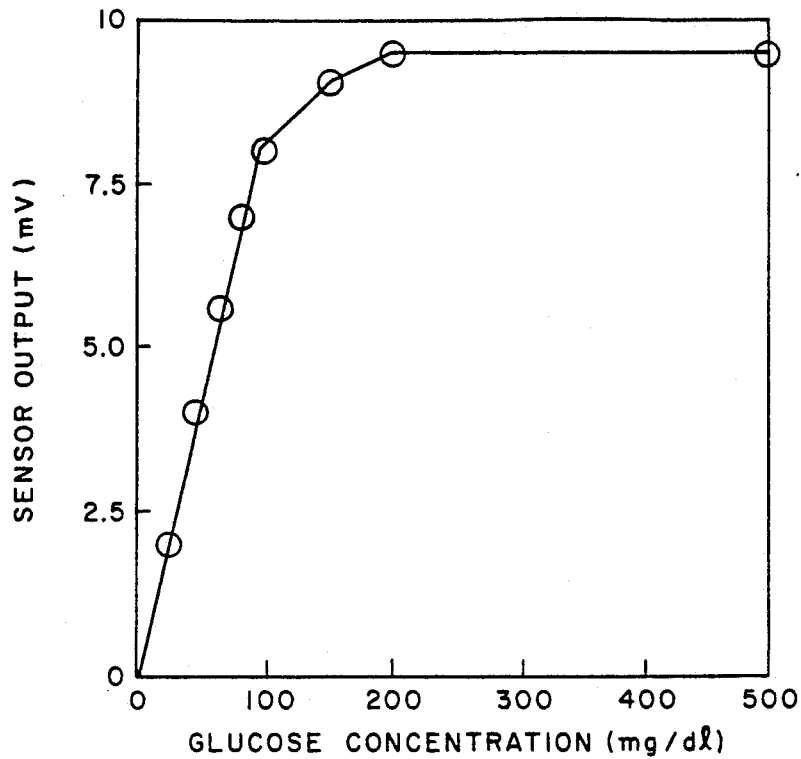
FIG. 3 is a graphic illustration of a calibration line similar to FIG. 2, but obtained by a prior art glucose sensor.

FIG. 2 shows a calibration line obtained by the thus prepared glucose sensor and FIG. 3 shows a calibration line obtained by a prior art glucose sensor prepared in the similar manner but not having the pH buffering agent in the enzyme-immobilized membrane and not having the permeation-restricted membrane. These calibration lines were obtained by using 20 mM HEPES-Na solution (pH 7.5; saturated by atmosphere) at 25° C.

As shown in FIG. 3, the prior art glucose sensor does not show a sensor output in proportion to glucose concentration in a glucose concentration range higher than 100 mg/dl and its output is saturated in a glucose concentration range higher than 150 mg/dl.

On the other hand, as shown in FIG. 2, the glucose sensor of the present invention shows an output proportional to glucose concentration up to 500 mg/dl glucose concentration.

It is thus clear that a broader determination range can be realized by the enzyme electrode of the present invention by combining the enzyme-immobilized membrane having the pH buffer capacity and the permeation-restricted membrane restricting permeation to analyte.

Figure 4:
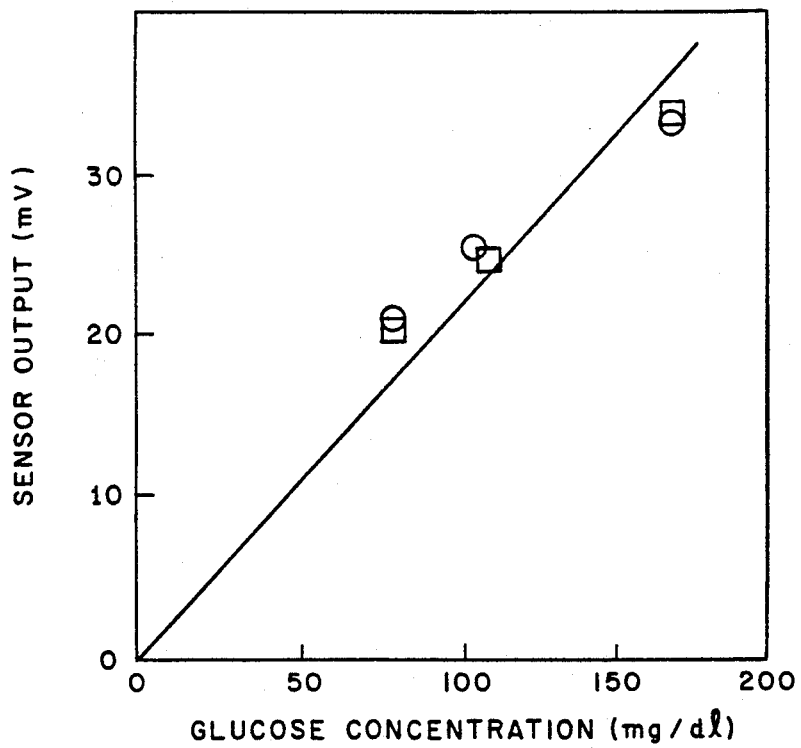
FIG. 4 is a graphic illustration of actual blood glucose determination data obtained by the glucose sensors of FIGS. 1(a) and 1(b).

By means of the glucose sensor of the present invention as above prepared, blood glucose concentrations were determined. Samples used were sera and their glucose concentrations were first determined by a precision clinical analyzer. Outputs of the glucose sensor of the present invention for the same samples were then measured. Output values after 1 minute reaction time are shown in FIG. 4 by circles, from which it is clear that sensor outputs proportional to glucose concentrations can be obtained by the glucose sensor of the present invention.

EXAMPLE 2

Figure 1:
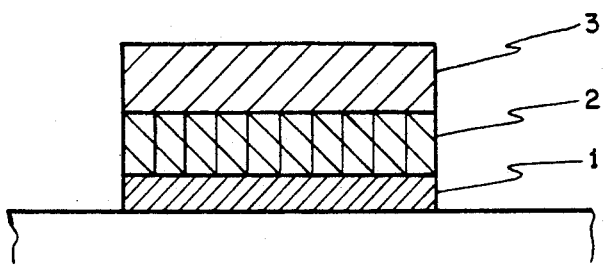
FIGS. 1(a) and 1(b) respectively show cross sectional views of embodiments of the enzyme electrode of the present invention in the form of glucose sensors.
Figure 1:
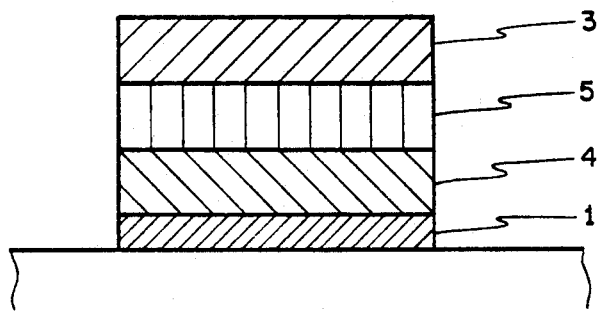

A glucose sensor similar to that of Example 1 was prepared. This glucose sensor has cross section as shown in FIG. 1 (b). First, a membrane 4 having pH buffer capacity was formed on a sensing portion of ISFET 1 by using a solution of composition as follows:
Bovine serum albumin: 30 mg
50 mM HEPES-Na solution (pH 7.5): 0.8 ml
5% glutaraldehyde aqueous solution: 0.2 ml Next, the membrane 4 was immersed in glutamic acid solution similarly to Example 1 and then an enzyme-immobilized membrane 5 was formed thereon by using a solution of the composition same as that shown in Example 1. Subsequently the membrane 5 was immersed in 0.1M glycine solution for 10 minutes to modify unreacted aldehyde groups to carboxyl groups. The thus prepared two-layer construction membrane was subjected to patterning by a lift-off method as in Example 1. Finally a permeation-restricted membrane 3 was formed thereon in the manner shown in Example 1.

By means of the glucose sensor prepared as above, serum samples were examined in the manner shown in Example 1. The results obtained are shown in FIG. 4 by squares.

EXAMPLE 3

An enzyme-immobilized membrane was prepared on ISFET in the manner same as Example 1 and was subjected to introduction of carboxyl groups in the manner similar to Example 1 but with use of 0.1M glycine solution in place of 0.1M glutamic acid solution used in Example 1.

Figure 5:
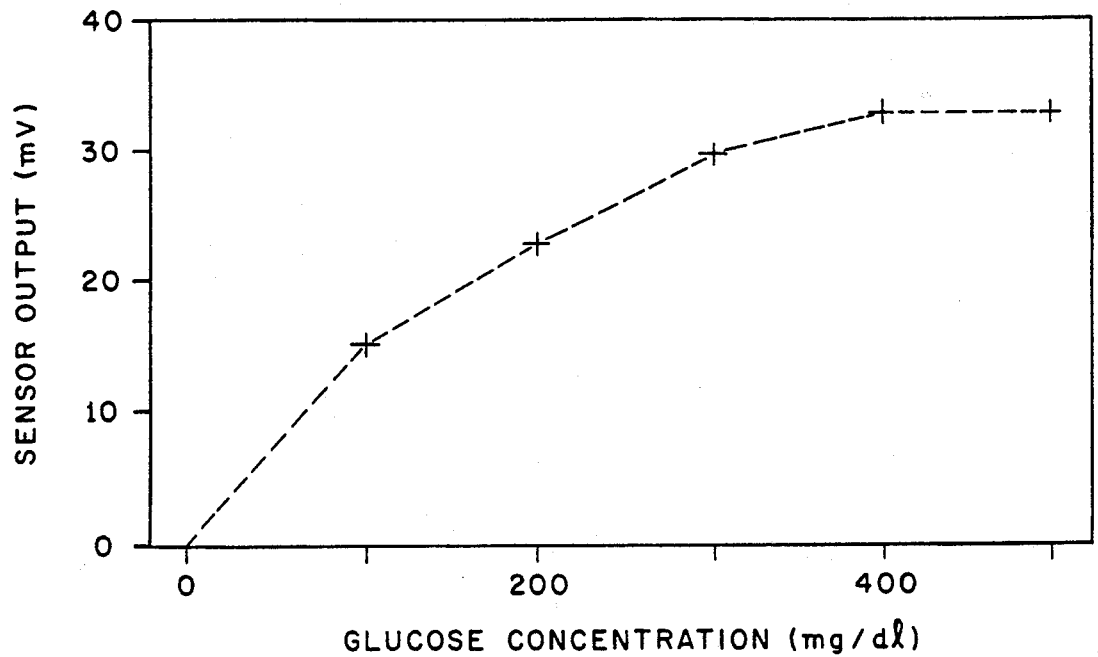
FIG. 5 is a graphic illustration of a calibration line similar to FIG. 2, but obtained by another embodiment of the enzyme electrode of the present invention in the form of a glucose sensor.

Then a permeation-restricted membrane was formed on the enzyme-immobilized and buffered membrane prepared as above by coating with albumin solution having composition as follows:
Bovine serum albumin: 12 mg
50 mM HEPES-Na buffer solution (pH 7.5): 0.6 ml
5% glutaraldehyde aqueous solution: 0.4 ml As to the glucose sensor thus prepared, a calibration line was prepared in the manner shown in Example 1. As shown in FIG. 5, the calibration line indicates that its sensor output is in proportion to glucose concentration up to 400 mg/dl glucose concentration and is not saturated until exceeding 500 mg/dl glucose concentration.

This glucose sensor having an albumin membrane as the permeation-restricted membrane and the glucose sensor having a silicone rubber membrane as the permeation-restricted membrane described in Example 1 were compared as to their durability, by repeating measurements of samples 100 times for each of 20 pieces of each of the glucose sensors of Examples 1 and 3. This durability tests showed that 90% of the sensors of this Example 3 retained ample enzyme activity and was usable for measurement after the tests, but 10 pieces of the sensors of Example 1 showed peeling-off of the silicon rubber membrane and only 8 of the remaining 10 pieces retrained enzyme activity.

It is thus clear that use of an albumin membrane crosslinked with glutaraldehyde as the permeation-restricted membrane realizes an enzyme electrode having a wide range of measurement and also high durability.

Figure 6A:
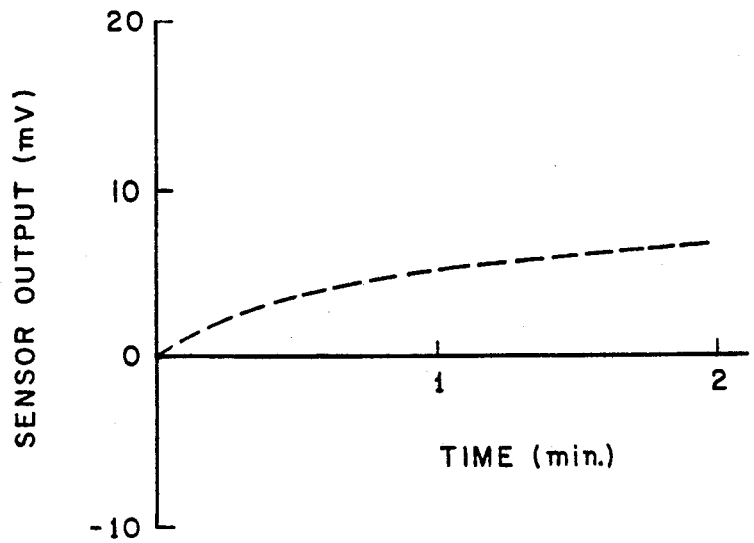
FIGS. 6(a) and 6(b) are graphic illustrations of response curves of a glucose sensor obtained respectively by the method of the present invention and the method of the prior art.
Figure 6B:
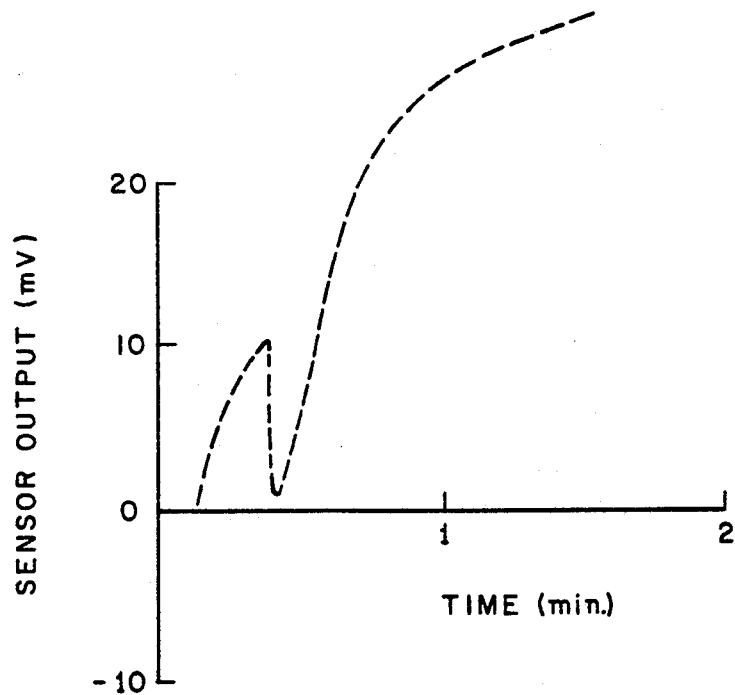

By means of the glucose sensor of this Example 3, blood glucose concentration was determined by a method of the present invention and a method of prior art. In the method of the present invention, the glucose sensor was immersed in a serum sample (25 µl) for 10 minutes and its output was measured. Then stirring was started by vibrating the sample or the sensor and its net output was continuously recorded from immediately after starting the stirring. In the prior art method, first the glucose sensor was immersed in buffer solution free from glucose and a background output was measured, and then the glucose sensor was immersed in a serum sample and its response was recorded. In FIGS. 6 (a) and 6 (b), response curves obtained by these two methods are shown respectively. FIG. 6 (b) shows that in the prior art method, noise is generated when the sensor is immersed in a serum sample and so measurement is difficult, whereas FIG. 6 (a) shows that in a method of the present invention, a good response curve is obtainable.

Figure 7:
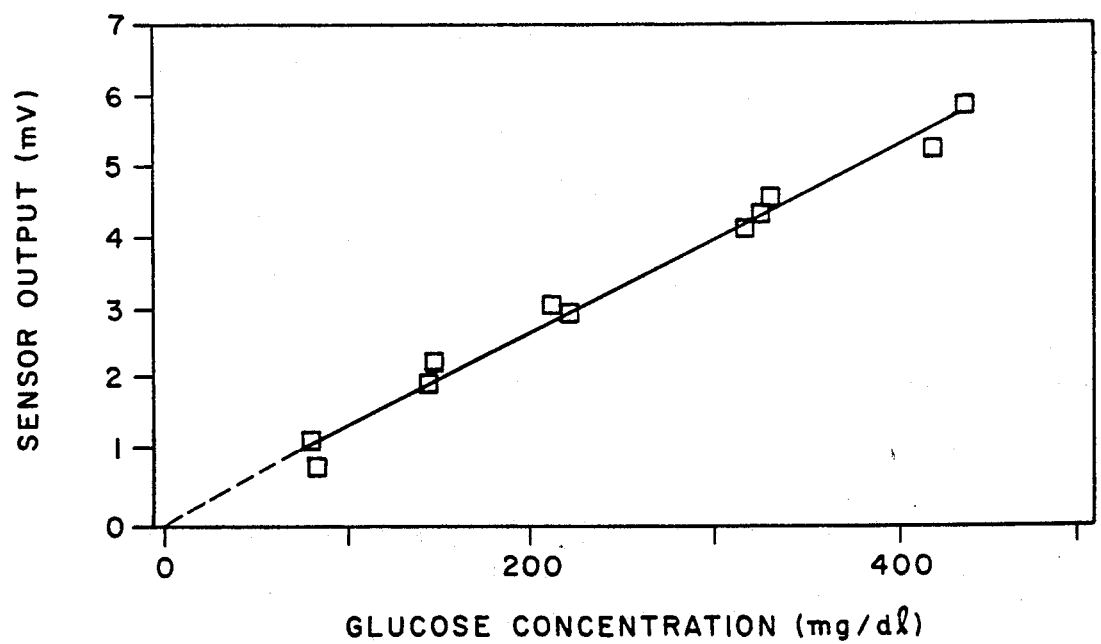
FIG. 7 is a graphic illustration of actual blood glucose determination data obtained by the method of the present invention.

By means of the glucose sensor of this Example 3 and in accordance with the method of the present invention, measurements were made on serum samples of various glucose concentrations. Relation of output differences between before stirring and after stirring obtained by the glucose sensor and glucose concentrations determined by a precise clinical analyzer is shown in FIG. 7, from which it is clear that wide range determination can be made without use of buffer solution for background measurement, in accordance with the method of the present invention.

As explained in detail as above, the present invention has enabled to determine high concentration of an analyte in a sample solution by an enzyme electrode, to improve durability of the enzyme electrode and to simplify the method of determining analyte concentration in a sample solution by an enzyme electrode.

I claim:
1. An enzyme electrode comprising:
 (a) an electrochemical transducer device for detecting variation of a phase boundary potential,
 (b) an enzyme-immobilized membrane wherein an enzyme and carboxyl groups are immobilized, said carboxyl groups acting as a buffering agent against an acid produced by an enzyme reaction, and
 (c) a permeation-restricted membrane having a restricted permeability to an analyte but having a good permeability to oxygen and being formed by material comprising an albumin crosslinked by glutaraldehyde;
 said enzyme-immobilized membrane (b) and permeation-restricted membrane (c) being formed on the surface of said electrochemical transducer device (a) in the named order.
2. An enzyme electrode comprising:

(a) an electrochemical transducer device for detecting variation of a phase boundary potential, (b) an enzyme-immobilized membrane formed by a layer (b1) of a material for immobilizing and containing carboxyl groups, said carboxyl groups acting as an agent for buffering against an acid produced by an enzyme reaction, and a layer (b2) of an immobilized enzyme, said layers (b1) and (b2) being formed on the surface of the electrochemical transducer device (a) in the named order, and (c) a permeation-restriction membrane having a permeability restricted to an analyte but having a good permeability relative to oxygen and being formed by material comprising an albumin crosslinked by glutaraldehyde;

said enzyme-immobilized membrane (b) and permeation-restricted membrane (c) being formed on the surface of said electrochemical transducer device (a) in the named order.

3. The enzyme electrode according to claim 1, wherein the enzyme-immobilized membrane (b) is formed by a layer (b1) of a material having pH buffer capacity and a layer (b2) of an immobilized enzyme, said layers (b1) and (b2) being formed on the surface of the electrochemical transducer device (a) in this order.

4. The enzyme electrode according to claim 2, wherein the layer (b2) of an immobilized enzyme includes glucose oxidase and gluconolactose as immobilized enzyme.

5. A method of determining a concentration of an analyte in a sample solution by means of an enzyme electrode comprising: (a) an electrochemical transducer device for detecting a variation of a phase boundary potential, (b) an enzyme-immobilized membrane wherein an enzyme and carboxyl groups are immobilized, said carboxyl groups acting as a buffering agent against an acid produced by an enzyme reaction, and (c) a permeation-restriction membrane having a restricted permeability to an analyte but having a good permeability relative to oxygen; said enzyme-immobilized membrane (b) and permeation-restricted membrane (c) being formed on the surface of said electrochemical transducer device (a) in the named order, which method comprises the steps of:

(i) immersing said enzyme electrode in the sample solution for a predetermined time period, (ii) stirring the sample solution, and (iii) measuring a difference of electrode outputs between before the stirring and after the stirring. to determine a concentration of the analyte in the sample solution.

* * * * *